United States Patent
Herweck et al.

(10) Patent No.: US 7,637,886 B2
(45) Date of Patent: Dec. 29, 2009

(54) EXPANDABLE FLUOROPOLYMER DEVICE AND METHOD OF MAKING

(75) Inventors: Steve A. Herweck, Nashua, NH (US); Peter H. Gingras, Windham, NH (US); Paul Martakos, Pelham, NH (US); Theodore Karwoski, Hollis, NH (US)

(73) Assignee: Atrium Medical Corporation, Hudson, NH (US)

( * ) Notice: Subject to any disclaimer, the term of this patent is extended or adjusted under 35 U.S.C. 154(b) by 70 days.

(21) Appl. No.: 10/131,396

(22) Filed: Apr. 22, 2002

(65) Prior Publication Data

US 2002/0183716 A1 Dec. 5, 2002

Related U.S. Application Data

(63) Continuation-in-part of application No. 09/410,329, filed on Oct. 1, 1999, now Pat. No. 6,395,208.

(60) Provisional application No. 60/117,152, filed on Jan. 25, 1999.

(51) Int. Cl.
*A61M 29/00* (2006.01)

(52) U.S. Cl. ............... 604/103.01; 604/103.06; 604/93.01

(58) Field of Classification Search ...... 604/93.01–120, 604/509; 525/166, 176, 179, 183, 496
See application file for complete search history.

(56) References Cited

U.S. PATENT DOCUMENTS 3,635,223 A 1/1972 Klieman ............ 128/348

(Continued)

FOREIGN PATENT DOCUMENTS

EP 293090 11/1988

(Continued)

OTHER PUBLICATIONS

Hwang et al. "Physiological transport forces govern drug distribution for stent-based delivery." *Circulation.* Jul. 31, 2001;104(5):600-5.

(Continued)

*Primary Examiner*—Nicholas D Lucchesi
*Assistant Examiner*—Laura A Bouchelle
(74) *Attorney, Agent, or Firm*—Lahive & Cockfield, LLP; Kevin J. Canning

(57) ABSTRACT

A radially expandable device having a body constructed of a generally inelastic, expanded fluoropolymer material is described. The body is deployable upon application of a radial expansion force from a reduced diameter, collapsed configuration to an expanded configuration having a predefined and fixed increased diameter. The body has a singular, unitary construction of generally homogenous material that is characterized by a seamless construction of expanded fluoropolymer material, such as expanded polytetrafluoroethylene (ePTFE), and is preferably constructed through an extrusion and expansion process. The body is further characterized by a microstructure of nodes interconnected by fibrils in which substantially all the nodes of the body are oriented generally perpendicularly to the longitudinal axis of the body. The monolithic construction of the body and the orientation of the nodes, perpendicular to the longitudinal axis of the body, yields a radially expandable device that predictably and dependably expands to a predefined, fixed maximum diameter that is generally independent of the expansion force used to radially expand the device. In addition, the microstructure of nodes interconnected by fibrils provides at least one predetermined flow rate of fluid therethrough over a range of fluid pressures.

37 Claims, 7 Drawing Sheets

U.S. PATENT DOCUMENTS

| | | | |
|---|---|---|---|
| 3,888,249 A | 6/1975 | Spencer | 128/214 |
| 3,901,232 A | 8/1975 | Michaels et al. | 128/260 |
| 3,981,299 A | 9/1976 | Murray | 128/349 |
| 4,030,503 A | 6/1977 | Clark, III | 128/304 |
| 4,229,838 A | 10/1980 | Mano | 3/1.4 |
| 4,327,721 A | 5/1982 | Goldin et al. | 128/207.15 |
| 4,338,942 A | 7/1982 | Fogarty | 128/344 |
| 4,406,656 A | 9/1983 | Hattler et al. | 604/280 |
| 4,417,576 A | 11/1983 | Baran | 128/207.15 |
| 4,423,725 A | 1/1984 | Baran et al. | 128/207.15 |
| 4,437,856 A | 3/1984 | Valli | 604/29 |
| 4,490,421 A | 12/1984 | Levy | 428/35 |
| 4,573,966 A | 3/1986 | Weikl et al. | 604/53 |
| 4,636,195 A | 1/1987 | Wolinsky | 604/53 |
| 4,637,396 A | 1/1987 | Cook | 128/344 |
| 4,650,466 A | 3/1987 | Luther | 604/95 |
| 4,692,200 A | 9/1987 | Powell | 156/289 |
| 4,693,243 A | 9/1987 | Buras | 128/207.15 |
| 4,711,251 A | 12/1987 | Stokes | 128/784 |
| 4,713,070 A | 12/1987 | Mano | 623/1 |
| 4,714,460 A | 12/1987 | Calderon | 604/28 |
| 4,714,461 A | 12/1987 | Gabel | 604/53 |
| 4,721,507 A | 1/1988 | Chin | 604/100 |
| 4,744,366 A | 5/1988 | Jang | 128/344 |
| 4,762,130 A | 8/1988 | Fogarty et al. | 128/348.1 |
| 4,799,479 A | 1/1989 | Spears | 128/303.1 |
| 4,820,349 A | 4/1989 | Saab | 128/344 |
| 4,824,436 A | 4/1989 | Wolinsky | 604/53 |
| 4,832,688 A | 5/1989 | Sagae et al. | 604/53 |
| RE32,983 E | 7/1989 | Levy | 428/36.92 |
| 4,850,969 A | 7/1989 | Jackson | 604/96 |
| 4,877,031 A | 10/1989 | Conway et al. | 128/344 |
| 4,935,190 A | 6/1990 | Tennerstedt | 264/529 |
| 4,957,669 A | 9/1990 | Primm | 264/23 |
| 4,968,306 A | 11/1990 | Huss et al. | 604/264 |
| 4,968,307 A | 11/1990 | Dake et al. | 604/264 |
| 4,994,033 A | 2/1991 | Shockey et al. | 604/101 |
| 5,015,232 A | 5/1991 | Maglinte | 604/96 |
| 5,021,044 A | 6/1991 | Sharkawy | 604/53 |
| 5,034,082 A | 7/1991 | Nolan | 156/245 |
| 5,041,090 A | 8/1991 | Scheglov et al. | 604/101 |
| 5,049,132 A | 9/1991 | Shaffer et al. | 604/101 |
| 5,061,276 A * | 10/1991 | Tu et al. | 623/1.33 |
| 5,071,424 A | 12/1991 | Reger | 606/159 |
| 5,087,244 A | 2/1992 | Wolinsky et al. | 604/53 |
| 5,087,247 A | 2/1992 | Horn et al. | 604/98 |
| 5,087,394 A | 2/1992 | Keith | 204/22 |
| 5,098,381 A * | 3/1992 | Schneider | 604/103.01 |
| 5,100,383 A | 3/1992 | Lichtenstein | 604/96 |
| 5,112,305 A | 5/1992 | Barath et al. | 604/96 |
| 5,112,347 A | 5/1992 | Taheri | 606/200 |
| 5,117,839 A * | 6/1992 | Dance | 600/585 |
| 5,156,610 A | 10/1992 | Reger | 606/159 |
| 5,176,638 A | 1/1993 | Don Michael | 604/101 |
| 5,192,290 A | 3/1993 | Hilal | 606/159 |
| 5,199,951 A | 4/1993 | Spears | 604/96 |
| 5,211,651 A | 5/1993 | Reger et al. | 606/159 |
| 5,213,576 A * | 5/1993 | Abiuso et al. | 604/103.01 |
| 5,232,444 A | 8/1993 | Just et al. | 604/96 |
| 5,236,659 A | 8/1993 | Pinchuk et al. | 264/573 |
| 5,254,089 A | 10/1993 | Wang | 604/96 |
| 5,267,985 A | 12/1993 | Shimada et al. | |
| 5,269,755 A | 12/1993 | Bodicky | 604/53 |
| 5,279,565 A | 1/1994 | Klein et al. | 604/105 |
| 5,282,484 A | 2/1994 | Reger | 128/898 |
| 5,282,785 A | 2/1994 | Shapland et al. | |
| 5,286,254 A | 2/1994 | Shapland et al. | 604/21 |
| 5,295,962 A | 3/1994 | Crocker et al. | 604/101 |
| 5,304,340 A | 4/1994 | Downey | 264/521 |
| 5,306,250 A * | 4/1994 | March et al. | 604/104 |
| 5,318,531 A | 6/1994 | Leone | 604/96 |
| 5,336,178 A * | 8/1994 | Kaplan et al. | 604/509 |
| 5,344,402 A | 9/1994 | Crocker | 604/96 |
| 5,368,566 A | 11/1994 | Crocker | 604/101 |
| 5,370,681 A * | 12/1994 | Herweck et al. | 623/1.27 |
| 5,397,307 A | 3/1995 | Goodin | 604/96 |
| 5,405,472 A | 4/1995 | Leone | 156/218 |
| 5,415,636 A | 5/1995 | Forman | 604/101 |
| 5,421,826 A | 6/1995 | Crocker et al. | 604/53 |
| 5,433,909 A | 7/1995 | Martakos et al. | 264/209.1 |
| 5,456,661 A | 10/1995 | Narciso | 604/20 |
| 5,458,568 A * | 10/1995 | Racchini et al. | 604/19 |
| 5,474,824 A | 12/1995 | Martakos et al. | 428/36.9 |
| 5,498,238 A | 3/1996 | Shapland et al. | |
| 5,499,971 A | 3/1996 | Shapland et al. | |
| 5,499,995 A | 3/1996 | Teirstein | 606/192 |
| 5,500,180 A | 3/1996 | Anderson et al. | 264/532 |
| 5,500,181 A | 3/1996 | Wang et al. | 264/532 |
| 5,512,051 A | 4/1996 | Wang et al. | 604/96 |
| 5,514,092 A | 5/1996 | Forman et al. | 604/101 |
| 5,522,800 A | 6/1996 | Crocker | 604/96 |
| 5,542,926 A | 8/1996 | Crocker | 604/102 |
| 5,569,198 A | 10/1996 | Racchini | |
| 5,628,730 A | 5/1997 | Shapland et al. | 604/21 |
| 5,634,899 A | 6/1997 | Shapland et al. | |
| 5,686,090 A * | 11/1997 | Schilder et al. | 424/423 |
| 5,707,385 A | 1/1998 | Williams | 606/192 |
| 5,709,653 A | 1/1998 | Leone | 604/20 |
| 5,713,853 A | 2/1998 | Clark et al. | 604/53 |
| 5,749,845 A * | 5/1998 | Hildebrand et al. | 604/21 |
| 5,752,934 A | 5/1998 | Campbell et al. | 604/96 |
| 5,772,632 A | 6/1998 | Forman | 604/101 |
| 5,782,797 A | 7/1998 | Schweich, Jr. et al. | 604/49 |
| 5,800,392 A | 9/1998 | Racchini | |
| 5,807,306 A | 9/1998 | Shapland et al. | 604/21 |
| 5,810,767 A | 9/1998 | Klein | 604/53 |
| 5,823,996 A | 10/1998 | Sparks | 604/96 |
| 5,833,659 A | 11/1998 | Kranys | 604/96 |
| 5,843,033 A | 12/1998 | Ropiak | 604/96 |
| 5,855,563 A * | 1/1999 | Kaplan et al. | 604/509 |
| 5,860,954 A | 1/1999 | Ropiak | 604/96 |
| 5,865,787 A | 2/1999 | Shapland et al. | |
| 5,868,704 A | 2/1999 | Campbell et al. | 604/96 |
| 5,868,719 A | 2/1999 | Tsukernik | 604/265 |
| 5,882,335 A | 3/1999 | Leone et al. | 604/96 |
| 5,902,266 A | 5/1999 | Leone et al. | 604/53 |
| 5,928,193 A | 7/1999 | Campbell | 604/96 |
| 5,935,667 A * | 8/1999 | Calcote et al. | 428/36.91 |
| 5,948,345 A | 9/1999 | Patel et al. | 264/529 |
| 6,013,055 A | 1/2000 | Bampos et al. | 604/96 |
| 6,039,755 A * | 3/2000 | Edwin et al. | 623/1.15 |
| 6,048,332 A | 4/2000 | Duffy et al. | 604/96 |
| 6,120,477 A * | 9/2000 | Campbell et al. | 604/96.01 |
| 6,135,982 A | 10/2000 | Campbell | 604/96.01 |
| 6,139,572 A | 10/2000 | Campbell et al. | 623/1.11 |
| 6,176,871 B1 * | 1/2001 | Pathak et al. | 623/1.21 |
| 6,217,565 B1 * | 4/2001 | Cohen | 604/525 |
| 6,248,092 B1 * | 6/2001 | Miraki et al. | 604/96.01 |
| 6,358,227 B1 | 3/2002 | Ferrera et al. | 604/103.06 |
| 6,369,039 B1 | 4/2002 | Palasis et al. | 514/44 |
| 6,375,637 B1 | 4/2002 | Campbell et al. | 604/103 |
| 6,450,989 B2 * | 9/2002 | Dubrul et al. | 604/104 |
| 6,451,047 B2 * | 9/2002 | McCrea et al. | 623/1.13 |
| 6,463,323 B1 | 10/2002 | Conrad-Vlasak et al. | |
| 6,500,174 B1 | 12/2002 | Maguire et al. | 606/41 |
| 6,730,016 B1 | 5/2004 | Cox et al. | |
| 6,902,522 B1 | 6/2005 | Walsh et al. | |
| 2002/0062147 A1 * | 5/2002 | Yang | 623/1.13 |
| 2002/0091435 A1 | 7/2002 | Campbell | 623/1.11 |
| 2002/0122903 A1 | 9/2002 | Ferrera et al. | 428/35.2 |

| | | | |
|---|---|---|---|
| 2002/0198521 A1 | 12/2002 | Maguire | 606/41 |

FOREIGN PATENT DOCUMENTS

| | | |
|---|---|---|
| EP | 0293090 A2 | 11/1988 |
| EP | 0293090 A3 | 11/1988 |
| EP | 383429 | 8/1990 |
| EP | 531117 | 3/1993 |
| EP | 0531117 B1 | 1/1997 |
| EP | 788774 | 8/1997 |
| EP | 835673 | 4/1998 |
| JP | 5-305146 | 11/1993 |
| WO | WO 87/06846 | 11/1987 |
| WO | WO 89/12478 | 12/1989 |
| WO | WO 90/01969 A1 | 3/1990 |
| WO | WO 91/08790 | 6/1991 |
| WO | WO 97/10871 | 3/1997 |
| WO | WO 97/17889 | 5/1997 |
| WO | WO 97/31590 | 9/1997 |
| WO | WO 97/31590 A1 | 9/1997 |
| WO | WO 98/26731 | 6/1998 |
| WO | WO 98/26731 A2 | 6/1998 |
| WO | WO 98/26731 A3 | 6/1998 |
| WO | WO 98/31415 | 7/1998 |
| WO | WO 98/33638 | 8/1998 |
| WO | WO 98/33638 A1 | 8/1998 |
| WO | WO 99/16500 | 4/1999 |
| WO | WO 01/24866 A1 | 4/2001 |
| WO | WO 01/80937 A1 | 11/2001 |
| WO | WO 02/22199 A2 | 3/2002 |
| WO | WO 02/22199 A3 | 3/2002 |

OTHER PUBLICATIONS

Oberhoff et al. "Local and systemic delivery of low molecular weight heparin following PTCA: acute results and 6-month follow-up of the initial clinical experience with the porous balloon (PILOT-study). Preliminary Investigation of Local Therapy Using Porous PTCA Balloons." *Cathet. Cardiovasc. Diagn.* Jul. 1998;44(3):267-74.

Lambert, C.R. et al., "Local drug delivery catheters: functional comparison of porous and microporous designs," *Current Science*, 4(5):469-475 (1993).

Wolinsky, H., "Historical perspective," *Semin Intervent Cardiol* 1:3-7 (1996).

\* cited by examiner

EXPANDABLE FLUOROPOLYMER DEVICE AND METHOD OF MAKING

REFERENCE TO RELATED APPLICATIONS

This application is a continuation in part application of application Ser. No 09/410,329, filed Oct. 1, 1999, which claimed priority to Provisional Application Ser. No. 60/117,152, filed Jan. 25, 1999, and both applications are hereby entirely incorporated herein by reference.

BACKGROUND OF THE INVENTION

Radially expandable devices are utilized in a wide range of applications, including a number of biological applications. Radially expandable devices in the form of inflatable balloons have been proposed for treatment of body passages occluded by disease and for maintenance of the proper position of catheter delivered medical devices within such body passages. Such expandable devices can be constructed of elastomeric materials such as latex.

A number of general problems are associated with such elastomeric balloons. Balloons and other expansion devices constructed of elastomeric materials can lack a maximum inflation or expansion diameter in that the prolonged application of an inflation medium will cause the balloon to continuously expand until the balloon bursts. Thus, over inflation of an elastomeric balloon may result in damage to the body vessel or organ being treated or may result in the balloon bursting within the body. Elastomeric balloons frequently do not inflate symmetrically and may not inflate to the desired size and shape. Asymmetrical expansion, as well as failure of the balloon to properly inflate, can lead to incomplete treatment of the body vessel. The high coefficient of friction of most elastomeric materials, such as latex, polyurethane, or silicone rubber, can result in damage to one or more cellular layers of the wall of the body vessel or organ being treated. Additionally, elastomeric expansion devices generally have insufficient strength for a number of applications, such as compressing adherent thrombus deposits formed on vascular walls and centering the catheter shaft away from the vessel wall.

Some elastomeric balloons include the feature of delivery of a liquid, such as a drug, to a targeted location. However, conventional balloons lack the ability to selectively control the rate of liquid passing through the walls of the balloon to the desired location within the patient. For example, the balloon can include a plurality of holes to allow a liquid inflating the balloon to pass through the balloon walls and be applied to a targeted location. However, if the balloon is required to be at full inflation to apply pressure to walls of a body lumen, the liquid used to inflate the balloon will pass through the plurality of holes at an increased rate, which may be undesireable.

Some applications of catheter balloons have incorporated design elements to permit an increased flow rate. One example is the use of a contrast agent injected into a lumen for aiding in radiographic viewing of a targeted location. Pressurized injections for viewing lumens, such as tubular vascular conduits, were subject to rapid washout and loss of the radiographic picture because of blood flow through the injected area. These catheters and injection systems were developed to permit for rapid bolus injections for diagnostic or therapeutic purposes. They were often utilized to obtain better visualization of structures, lesions, and narrowed areas, and allowed improved diagnostic information to be obtained.

More recently, improved imaging technology has enabled a number of viewing techniques, such as digital subtraction, advanced contrast, and lowered requirements for x-rays and exposure. In turn, more complete pictures, with improved resolution, have been obtained with less contrast media being introduced to the target location.

However, such advances have not yet adequately addressed the issue of introducing contrast media to view small, diseased or damaged, vessels, that are either in areas that are difficult to access, or are minor branches from larger flowing vessels.

SUMMARY OF THE INVENTION

The present invention provides a radially expandable device having a body constructed a fluoropolymer material, such as expanded polytetrafluoroethylene ("ePTFE"). The use of fluoropolymer materials provides a radial expandable device having a biocompatible and inelastic construction that is suitable for numerous uses including the treatment of body vessels, organs, and implanted grafts. The body of the radially expandable device has a longitudinal axis and a wall having a thickness transverse to the longitudinal axis. The wall of the body is characterized by a microstructure of nodes interconnected by fibrils, such that the microstructure of nodes interconnected by fibrils has one or more predetermined porosities suitable for regulating a flow of fluid therethrough at one or more substantially constant flow rates for a range of fluid pressures. Alternatively, the porosities can be suitable for regulating a flow of fluid therethrough in a manner such that a percentage of change of flow rates is substantially smaller for a given percentage of change of pressures. The porosity, or channel size, can be altered during manufacturing to result in a microstructure having a predetermined rate of fluid flow therethrough. The porosities at different locations along the microstructure can be made to differ to result in non-uniform porosity, or having more than one predetermined porosity along a single microstructure of nodes and fibrils. The body of the radially expandable device is deployable from a reduced diameter, collapsed configuration to an increased diameter, expanded configuration upon application of an expansion force to the radially expandable device. Along at least a portion of the body, substantially all the nodes of the microstructure are oriented generally perpendicularly to the longitudinal axis of the body. This orientation of the nodes, perpendicular to the longitudinal axis of the body, yields a radially expandable device that predictably and dependably expands to the increased diameter configuration.

The radially expandable device is suitable for preventing forward washout of an injected contrast agent, while also permitting low pressure perfusion of the contrast agent or dye, to allow for visualization of target locations. In addition, the radially expandable device is suitable for applying a minimally occlusive pressure in combination with low pressure contrast agent or dye injection to minimize or mitigate vessel damage due to dissection or wall jetting associated with high pressure injections. By controlling the porosity and creating channels of variable porosities through the device wall, the teachings of the present invention provide occlusive and low pressure release that can be modified for different structures, vessels, blood flow areas, or other target locations.

According to one aspect of the present invention, the radially expandable device can make use of, and be coupled with, a guide wire. The guide wire is utilized in positioning the radially expandable device within a patient body.

According to one aspect of the present invention, the body of the radially expandable device has a monolithic construction. The term "monolithic", as used herein, includes structures having a singular, unitary construction of generally homogenous material. The monolithic body of the radially expandable device of the present invention is characterized by a seamless construction of fluoropolymer material, such as expanded polytetrafluoroethylene (ePTFE), preferably constructed through an extrusion and expansion process. Because the cross section of the monolithic body is singular or unitary, the expandable device lacks seams or internal interfaces between adjacent layers that can result in unreliable expansion of the device. The monolithic construction of the body of the present invention contributes to the dependable and predictable expansion of the body to a predefined, fixed maximum diameter that is generally independent of the expansion force used to radially expand the device.

In accordance with a further aspect of the present invention, a method is provided for manufacturing a radially expandable device constructed of a fluoropolymer material such as, for example, expanded polytetrafluoroethylene (ePTFE). The method includes the step of forming a tube of fluoropolymer material having an initial diameter. A radial expansion force is applied to the tube to expand the tube from the initial diameter to a second diameter. The expansion force is then removed. The resultant tube is radially expandable from a reduced diameter to the second diameter upon application of a radial deployment force from a deployment mechanism within the tube. The deployment mechanism can be, for example, a fluid injected into the tube or a radial expansion element inserted into the tube.

A radially expandable device constructed in accordance with the method of the present invention can be dependably and predictably expanded to the second diameter upon the application of a radially deployment force within the tube. The second diameter can be predefined and fixed to a maximum expansion diameter through the manufacturing process of the present invention, resulting in an expansion device having a maximum expansion diameter that is generally independent of the radial deployment force applied to the device.

The fluoropolymer tube can be constructed through an extrusion and expansion process including the step of creating a billet by blending a mixture of a fluoropolymer and a lubricant and compressing the mixture. The fluoropolymer is preferably PTFE. The billet can then be extruded to form an extruded article. The lubricant is removed and the extruded article is expanded to form a monolithic tube of inelastic, expanded fluoropolymer material. The stretched tube is then heat set to lock in the microstructure of the tube and maintain the tube in the stretched state. The microporous through-pores can be made such that the rate at which fluid permeates through the microporous through-pores is substantially constant over a range of fluid pressures. The microporous through-pores can vary along a portion of tube to result in different constant fluid permeation rates at different locations along the tube. Alternatively, the microporous through-pores can be made such that the flow rate increases or decreases at a smaller percentage than the fluid pressure increases or decreases. In other words, a larger range of changes in pressure results in a smaller range of changes in flow rate through the microporous through-pores.

The extruded article is preferably bilaterally stretched in two opposing directions along the longitudinal axis of the article. Bilaterally stretching the extruded article yields an article that is substantially uniformly stretched over a major portion of its length and has a microstructure of nodes interconnected by fibrils. The bilateral stretching step can be carried out by displacing the ends of the extruded article either simultaneously or sequentially. The longitudinal stretch ratio of the expanded tube, i.e., the ratio of the final stretched length of the tube to the initial length, and the diametric stretch ratio, i.e., the ratio of the final diameter, after longitudinal stretching, and the initial diameter, can be varied to yield an expansion device having differing radial expansion properties. For example, the magnitude of the deployment force necessary to expand the expansion device of the present invention can be pre-selected and manipulated by varying the stretch ratios of the fluoropolymer tube. Additionally, the stretch rate can be varied to selectively provide the expansion device with improved expansion characteristics.

In accordance with another aspect of the present invention, the step of applying a radial expansion force to the fluoropolymer tube is carried out by inserting a balloon into the tube and expanding the balloon to apply the radial expansion force to the tube. Preferably, the balloon is constructed from an inelastic material such as, for example, polyethylene terephthalate (PET) or nylon. In a preferred embodiment, the balloon is constructed to be expandable to a predefined size and shape by inflation with a fluid. Radial expansion of the fluoropolymer tube with such an inelastic balloon imparts the predetermined size and shape of the balloon to the expanded fluoropolymer balloon.

In accordance with a further aspect of the present invention, the step of radially expanding the fluoropolymer tube plastically deforms the tube beyond its elastic limit to the second diameter. Plastically deforming the fluoropolymer tube to the second diameter contributes to expansion device dependably expanding to the second diameter upon application of the radial deployment force.

The step of radially expanding the fluoropolymer tube can also include the steps of positioning the tube within the internal cavity of a mold fixture and radially expanding the balloon within the tube while the tube remains positioned in the internal mold cavity. The internal mold cavity preferably has a size and shape analogous to the predefined size and shape of the balloon. The internal cavity of the mold facilitates concentric radial expansion of the balloon and the fluoropolymer tube.

In accordance with another aspect of the present invention, the step of applying a radial expansion force to the fluoropolymer tube is carried out by inserting a second tube constructed from an extruded inelastic material, such as extruded PET, into the fluoropolymer tube and expanding the second tube to apply the radial expansion force to the tube. Preferably, the fluoropolymer tube and the second tube are heated to a temperature less than or equal to the glass transition temperature of the extruded material forming the second tube during the radial expansion step. The heating of the tubes can be accomplished by submerging the tubes into a hot water bath. Alternatively, the fluoropolymer tube can be expanded by the second tube within a heated mold.

In accordance with a further aspect of the present invention, the radially expandable device of the present invention is particularly suited for treatment of body passages occluded by disease. The expandable device can be utilized in the manner of a catheter balloon suitable for deployment within a body vessel by a catheter. Exemplary treatment applications of the present application include dilation of stenoic blood vessels in a percutaneous transluminal angioplasty procedure (PTA), removal of thrombi and emboli from obstructed blood vessels, urethra dilation to treat prostatic enlargement due to benign prostate hyperplasia (BPH) or prostatic cancer, and generally restoring patency to implanted grafts or body passages such as blood vessels, the urinary tract, the intestinal tract, the kidney ducts, or other body passages.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION

Figure 1:
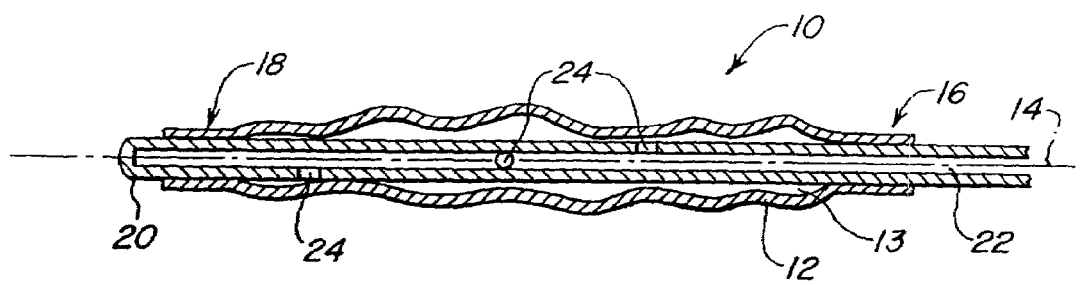
FIG. 1 is a side elevational view in cross-section of a radially expandable device according to the teachings of the present invention, illustrating the device in a first, reduced diameter configuration.
Figure 2:
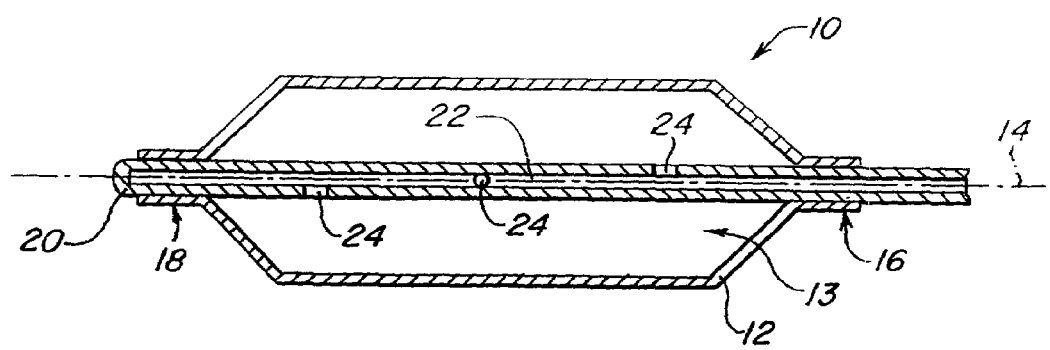
FIG. 2 is a side elevational view in cross-section of the radially expandable device of FIG. 1, illustrating the device in a second, increased diameter configuration.

A radially expandable device 10 having a shaped form, such as body 12 constructed of a generally inelastic, expanded fluoropolymer material is illustrated in FIGS. 1 and 2. Expandable devices provided by the present invention are suitable for a wide range of applications including, for example, a range of medical treatment applications. Exemplary biological applications include use as a catheter balloon for treatment of implanted grafts and body passages such as blood vessels, the urinary tract, the intestinal tract, kidney ducts, etc. Specific examples include as a device for the removal of obstructions such as emboli and thrombi from blood vessels, as a dilation device to restore patency to an occluded body passage as an occlusion device to selectively obstruct a body passage, and as a centering mechanism for transluminal instruments and catheters. The expandable device of the present invention can also be used as a sheath for covering conventional catheter balloons to control the expansion of the conventional balloon.

The body 12 of the radially expandable device 10 is deployable upon application of an expansion force from a first, reduced diameter configuration, illustrated in FIG. 1, to a second, increased diameter configuration, illustrated in FIG. 2. The body 12 of the expansion device 10 of the present invention preferably features a monolithic construction, i.e., the body 12 is a singular, unitary article of generally homogeneous material. The body 12 is manufactured in accordance with the methods of manufacturing of the present invention, an extrusion and expansion process described in detail below, to yield a body 12 characterized by a seamless construction of inelastic, expanded fluoropolymer. The fluoropolymer has a predefined size and shape in the second, increased diameter configuration. The body 12 can be dependably and predictably expanded to the predefined, fixed maximum diameter and to the predefined shape independent of the expansion force used to expand the device.

Referring specifically to FIG. 2, the body 12 of the radial expansion device 10 of the present invention is preferably generally tubular in shape when expanded, although other cross sections, such as rectangular, oval, elliptical, or polygonal, can be utilized. The cross section of the body 12 is preferably continuous and uniform along the length of the body. However, in alternative embodiments, the cross section can vary in size and/or shape along the length of the body. FIG. 1 illustrates the body 12 relaxed in the first, reduced diameter configuration. The body 12 has a central lumen 13 extending along a longitudinal axis 14 between a first end 16 and second end 18.

A deployment mechanism in the form of an elongated hollow tube 20 is shown positioned within the central lumen 13 to provide a radial deployment or expansion force to the body 12. The radial deployment force effects radial expansion of the body 12 from the first configuration to the second increased diameter configuration illustrated in FIG. 2. The first end 16 and the second end 18 are connected in sealing relationship to the outer surface of the hollow tube 20. The first and second ends 16 and 18 can be thermally bonded, bonded by means of an adhesive, or attached by other means suitable for inhibiting fluid leakage from the first and second ends 16 and 18 between the walls of the body 12 and the tube 20.

The hollow tube 20 includes an internal, longitudinal extending lumen 22 and a number of side-holes 24 that provide for fluid communication between the exterior of the tube 20 and the lumen 22. The tube 20 can be coupled to a fluid source (not shown) to selectively provide fluid, such as water, saline, or air, to the lumen 13 of the body 12 through the lumen 22 and side-holes 24. The pressure from the fluid provides a radial expansion force on the body 12 to radially expand the body 12 to the second, increased diameter configuration. Because the body 12 is constructed from an inelastic material, uncoupling the tube 20 from the fluid source or otherwise substantially reducing the fluid pressure within the lumen 13 of the body 12, does not generally result in the body 12 returning to the first, reduced diameter configuration. However, the body 12 will collapse under its own weight to a reduced diameter. Application of negative pressure, from, for example, a vacuum source, can be used to completely deflate the body 12 to the initial reduced diameter configuration.

One skilled in the art will appreciate that the expansion device 10 of the present invention is not limited to use with deployment mechanisms employing a fluid deployment force, such as hollow tube 20. Other known deployment mechanisms can be used to radially deploy the expansion device 10 including, for example, mechanical operated expansion elements, such as mechanically activated members or mechanical elements constructed from temperature activated materials such as nitinol.

Various fluoropolymer materials are suitable for use in the present invention. Suitable fluoropolymer materials include, for example, polytetrafluoroethylene ("PTFE") or copolymers of tetrafluoroethylene with other monomers may be used. Such monomers include ethylene, chlorotrifluoroethylene, perfluoroalkoxytetrafluoroethylene, or fluorinated propylenes such as hexafluoropropylene. PTFE is utilized most often. Accordingly, while the radial expansion device 10 can be manufactured from various fluoropolymer materials, and the manufacturing methods of the present invention can utilize various fluoropolymer materials, the description set forth herein refers specifically to PTFE.

A method of manufacturing a radially expandable device in accordance with the present invention will be described in connection with FIGS. 4A-4C and the flow chart shown in FIG. 6A. The radially expandable device 10 of the present invention is produced from a tube 110 constructed of expanded fluoropolymer material, which is preferably produced through an extrusion and a longitudinal expansion process. The preferred fluoropolymer material is expanded PTFE (ePTFE), which is a hydrophobic, biocompatible, inelastic material having a low coefficient of friction, although, as discussed above, other inelastic, biocompatible fluoropolymer materials may be used.

To produce the ePTFE tube, a billet comprising a PTFE resin mixed with an organic lubricant is utilized. Various organic lubricants are suitable such as naphtha, ISOPAR-G and ISOPAR-H available from Exxon Corporation. The blended resin is compressed at low pressure to yield a tubular billet of PTFE resin and lubricant, step 210 of FIG. 6A. The tubular billet is then extruded through an extruder, for example a ram extruder, to reduce the cross section of the billet and to yield a tubular extrudate, step 212. The organic lubricant can be removed from the extrudate by drying the extrudate in a heated oven, step 214.

Once the tubular extrudate is produced, the extrudate is expanded by longitudinal stretching, step 216. Preferably, the extrudate is bilaterally stretched. Bilateral stretching is accomplished by displacing both ends of the extrudate, sequentially or simultaneously, away from the center of the extrudate. Bilateral stretching provides a material that is homogeneously stretched over the majority of its length. After the extrudate has been stretched, it is heat set to lock in the microstructure of the material, step 218 of FIG. 6A, and to complete the process of the forming the tube 110 of ePTFE.

Figure 3:
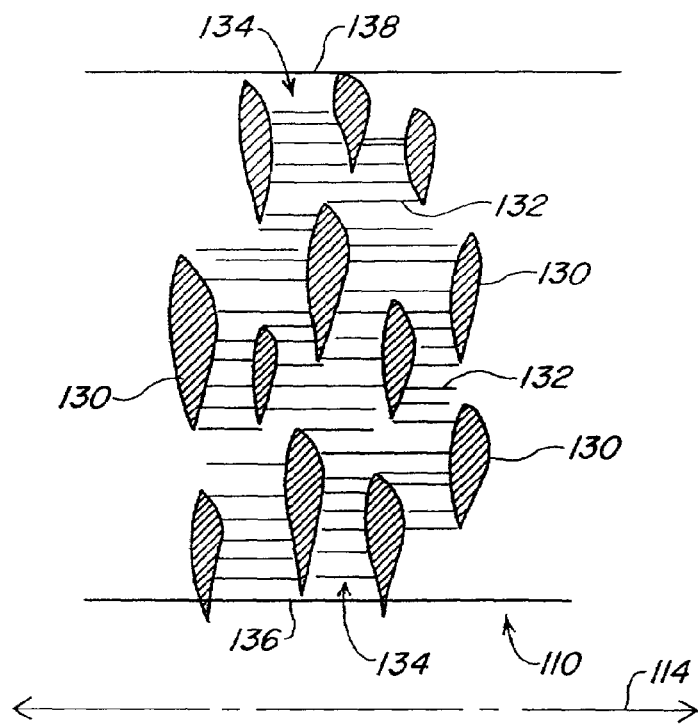
FIG. 3 is a schematic representation of the microstructure of a section of the wall of an expanded fluoropolymer tube used during the manufacturing process of the present invention to yield the radially expandable device of the present invention.

FIG. 3 is a schematic representation of the microstructure of the walls of the ePTFE tube 110 as formed by the extrusion and expansion process described above. For purposes of description, the microstructure of the tube 110 has been exaggerated. Accordingly, while the dimensions of the microstructure are enlarged, the general character of the illustrated microstructure is representative of the microstructure prevailing within the tube 110.

The microstructure of the ePTFE tube 110 is characterized by nodes 130 interconnected by fibrils 132. The nodes 130 are generally oriented perpendicular to the longitudinal axis 114 of the tube 110. This microstructure of nodes 130 interconnected by fibrils 132 provides a microporous structure having microfibrillar spaces which define through-pores or channels 134 extending entirely from the inner wall 136 and the outer wall 138 of the tube 110. The through-pores 134 are perpendicularly oriented (relative to the longitudinal axis 114), internodal spaces that traverse from the inner wall 136 to the outer wall 138. The size and geometry of the through-pores 134 can be altered through the extrusion and stretching process, as described in detail in Applicants' copending U.S. patent application Ser. No. 09/411,797, filed on Oct. 1, 1999, which is incorporated herein by reference, and further described below, to yield a microstructure that is impermeable, semi-impermeable, or permeable.

The size and geometry of the through-pores 134 can be altered to form different orientations. For example, by twisting or rotating the ePTFE tube 110 during the extrusion and/or stretching process, the micro-channels can be oriented at an angle to an axis perpendicular to the longitudinal axis 114 of the tube 110. The expandable device 10 results from the process of extrusion, followed by stretching of the polymer, and sintering of the polymer to lock-in the stretched structure of through-pores 134.

In accordance with one embodiment, the ePTFE tube 110, and the resultant expandable device 10, has a fine nodal structure that is uniform throughout the cross section and length of the ePTFE tube. The uniform fine nodal structure provides the expandable device 10 with improved expansion characteristics as the expandable device dependably and predictably expands to the second diameter. The fine nodal structure can be characterized by nodes having a size and mass less than the nodes found in conventional ePTFE grafts, for example in the range of 25 μm-30 μm. Additionally, the spacing between the nodes, referred to as the internodal distance, and the spacing between the fibers, referred to as the interfibril distance, can also be less than found in conventional ePTFE grafts, for example in the range of 1 μm-5 μm. Moreover, the internodal distance and the interfibril distance in the preferred embodiment can be uniform throughout the length and the cross section of the ePTFE tube. The uniform nodal structure can be created by forming the billet with a uniform lubricant level throughout its cross section and length. Stretching the tubular extrudate at higher stretch rates, for example at rates greater than 1 in/s, yields the fine nodal structure. Preferably, the extrudate is stretched at a rate of approximately 10 in/s or greater. The nodal structure can also be non-uniform, by varying the location and amount of lubrication and stretching processes.

In the instance of the fluid inflating the body 12 of the radially expandable device 10, the fluid can pass through the body 12 in a weeping manner, and be applied to a target location in the patient body. The fluid, in such an instance, can contain one or more drugs having therapeutic properties for healing the affected target location. Example drugs can include those listed in Table 1 below.

TABLE 1

| Class | Examples |
| --- | --- |
| Antioxidants | Lazaroid, Probucol, Vitamin E |
| Antihypertensive Agents | Diltiazem, Nifedipine, Verapamil |
| Antiinflammatory Agents | Glucocorticoids, Cyclosporine, NSAIDS |
| Growth Factor Antagonists | Angiopeptin, trapidil, suramin |
| Antiplatelet Agents | Aspirin, Dipyridamole, Ticlopidine, Clopidogrel, GP IIb/IIIa inhibitors, Abciximab |
| Anticoagulant Agents | Heparin (low molecular weight and unfractionated), Wafarin, Hirudin |
| Thrombolytic Agents | Alteplase, Reteplase, Streptase, Urokinase, TPA |
| Drugs to Alter Lipid Metabolism (e.g. statins) | Fluvastatin, Colestipol, Lovastatin |
| ACE Inhibitors | Elanapril, Fosinopril, Cilazapril |
| Antihypertensive Agents | Prazosin, Doxazosin |
| Antiproliferatives and Antineoplastics | Cochicine, mitomycin C, Rapamycin, taxols, Everolimus, Tacrolimus, Sirolimus |
| Tissue growth stimulants | Bone morphogeneic protein, fibroblast growth factor |
| Gasses | Nitric oxide, Super Oxygenated $O_2$ |
| Promotion of hollow organ occlusion or thrombosis | Alcohol, Surgical Sealant Polymers, Polyvinyl particulates, 2-Octyl Cyanoacrylate, Hydrogels, Collagen |
| Functional Protein/Factor Delivery | Insulin, Human Growth Hormone, Estrogen, Nitric Oxide |
| Second messenger targeting | Protein kinase inhibitors |
| Angiogenic | Angiopoetin, VEGF |
| Anti-Angiogenic | Endostatin |
| Inhibition of Protein Synthesis | Halofuginone |
| Antiinfective Agents | Penicillin, gentamycin |
| Gene Delivery | Genes for Nitric Oxide Synthase, human growth hormone, antisense oligonucleotides |
| Local Tissue Perfusion | Alcohol, $H_2O$, Saline, Hot or Cold $H_2O$ for thermal ablation |
| Nitric Oxide Donating Derivatives | NCX 4016-Nitric Oxide donating derivative of Aspirin |
| Contrast Media | |

The teachings of the present invention enable the variation of the internodal distance and the interfibral distance can be varied to control over a larger range, to allow a fluid to pass through the through-pores or channels 134. The size of the through-pores or channels 134 can be selected through the manufacturing process of the present invention, described in detail in U.S. patent application Ser. No. 09/411,797, previously incorporated herein by reference. The internodal distance of microstructure of the wall within the microporous region, and hence the width of the through-pores or channels 134, can be approximately 1 μm to approximately 150 μm. Internodal distances of this magnitude can yield flow rates of approximately 0.01 ml/min to approximately 100 ml/min of fluid through the wall of the body 12.

The internodal distances can also vary at different locations along the microporous structure to result in the channels 134 being of different sizes in different locations or regions. This enables different flow rates to occur through different areas of the same microporous structure at a same fluid pressure.

The different flow rates achieved by the radially expandable device 10 enable variations in fluid pressure during inflation of the expandable device 10, and also enable a variation in dwell time of the expandable device 10 at a target location requiring therapeutic treatment. Dwell time is a measurement of the amount of time the expandable device 10 is disposed within the patient body applying one or more therapeutic agents to a location within the patient body, such as a target location. The target location is a location requiring therapeutic treatment. The ability to vary the size and shape of the through-pores or channels 134 enables modification of the dwell time. If a longer dwell time is desired, the size and shape of the through-pores 134 can be varied to allow less fluid to pass through. Likewise, if a shorter dwell time is desired with the same amount of therapeutic fluid to be applied, the through-pores 134 can be varied to allow more fluid to pass through at a faster rate.

The microporous structure of the through-pores 134 is such that the fluid pressure of the fluid passing through can vary over a substantial range and still result in substantially the same rate of fluid flow through the through-pores 134. For example, for a predetermined range of fluid pressures, the rate of fluid flow through the through-pores 134 remains substantially constant for a given embodiment. Alternatively, the percentage of change of the rate of fluid flow can be made less than a given percentage of change of fluid pressure. This enables the fluctuation of fluid pressure to increase or decrease the rigidity of the expandable device 10, without substantially affecting the rate at which the fluid, including therapeutic drug, passes through the through-pores 134.

Figure 4A:
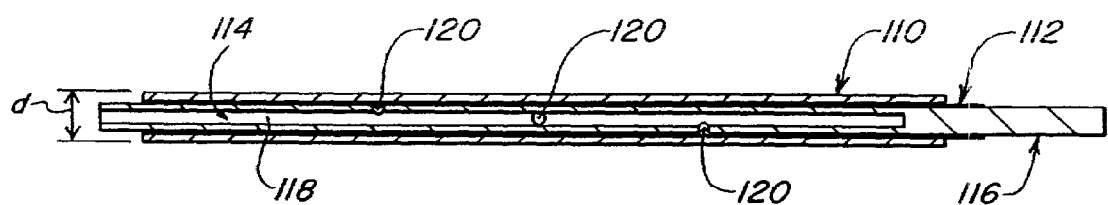
FIG. 4A is a side elevational view in cross-section of an inelastic balloon positioned within an expanded fluoropolymer tube, illustrating the inelastic balloon in a deflated condition in accordance with a method of manufacturing a radially expandable device according to the teachings of the present invention.
Figure 6A:
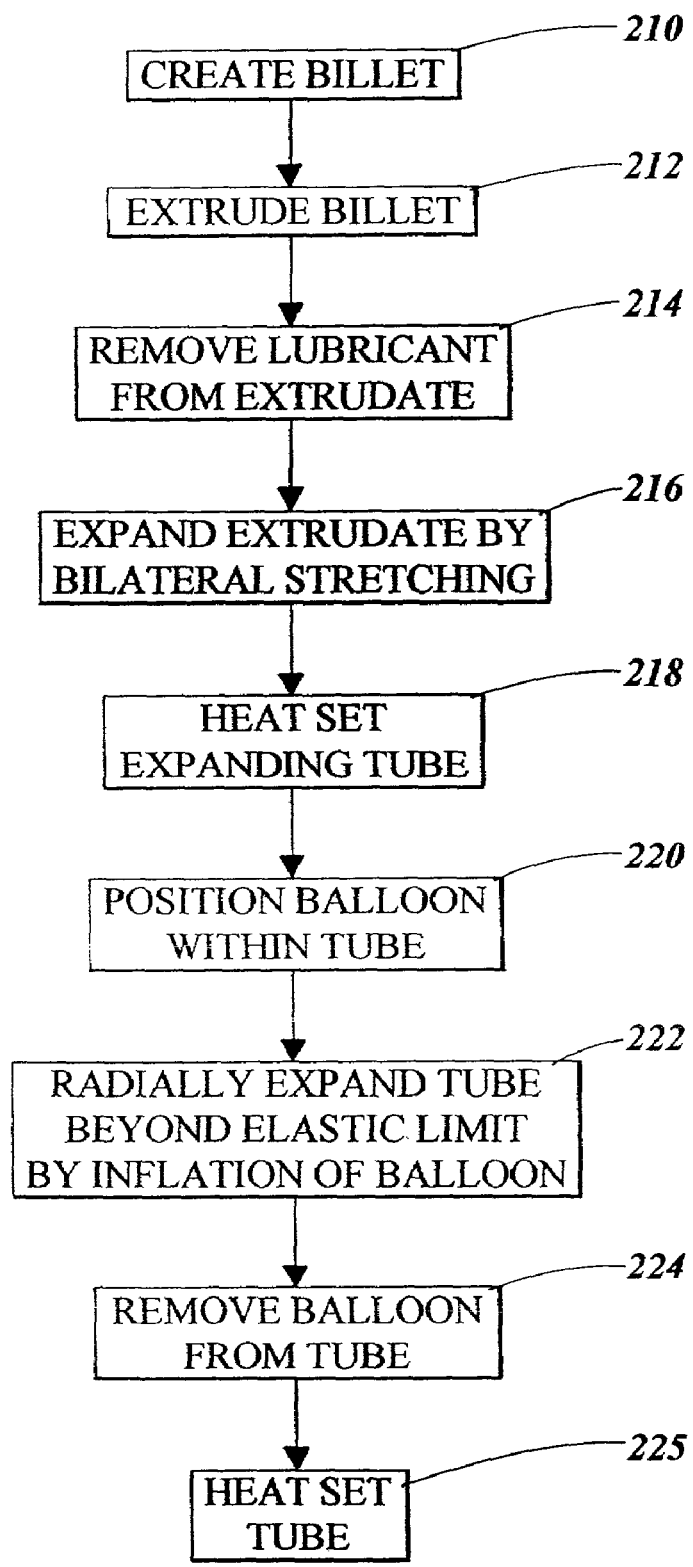
FIG. 6A is a flow chart illustrating the steps of manufacturing a radially expandable device according to the teachings of the present invention.

Continuing to describe the manufacturing method of the present invention and referring to FIGS. 4A and 6A, the ePTFE tube 110, having an initial diameter d, is pulled over a balloon 112 to position the balloon 112 within the lumen 114 of the tube 110, step 220 of FIG. 6A. The balloon 112 is preferably constructed of an inelastic material such as, for example, PET or nylon, such that the balloon 112, when inflated, attains a predetermined size and shape. The balloon 112 can be bonded or otherwise coupled to a rigid catheter or hypo-tube 116 to facilitate placement and removal of the ePTFE tube as described below. The catheter 116 has a central inflation lumen 118 and a plurality of side-holes 120 to provide for the delivery of an inflation fluid to inflate the balloon 112.

Figure 4B:
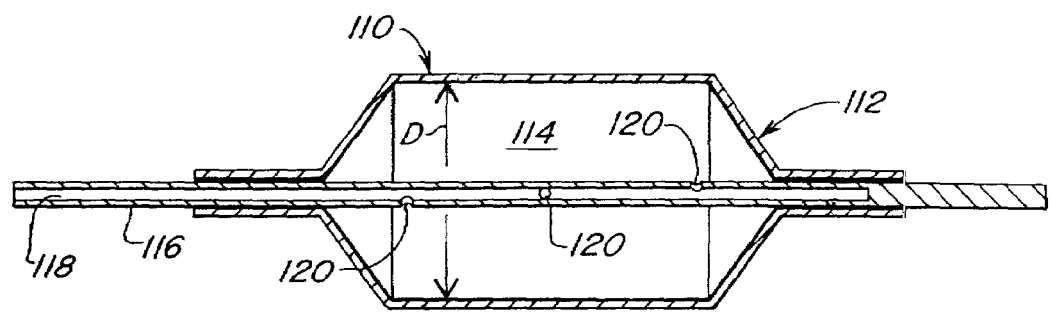
FIG. 4B is a side elevational view in cross-section of the inelastic balloon and the expanded fluoropolymer tube of FIG. 4A, illustrating the inelastic balloon in an inflated condition in accordance with a method of manufacturing a radially expandable device according to the teachings of the present invention.

Referring specifically to FIG. 4B, the balloon 112 can be inflated by introduction of a pressurized fluid to the lumen 114 of the ePTFE tube 110. The overlying ePTFE tube 110 expands with the inelastic balloon 122 until both the balloon 112 and the ePTFE tube 110 obtain the predetermined size and shape of the inflated balloon 112, step 222 of FIG. 6A. The inflated balloon 112 thus imparts its predetermined size and shape to the ePTFE tube 110. This radially expansion process is referred to as blow-molding. The PTFE tube 110 shown in FIG. 4B is radially expanded from the initial diameter d (FIG. 4A) to an increased diameter D. This radial expansion process may take place in an air, water, or steam-heated chamber that is heated to a temperature between 35° C. and 60° C., preferably 50° C. The elevated temperature can contribute to uniform expansion, both circumferentially and longitudinally, of the ePTFE balloon, as well as uniform wall thickness.

It is preferable for the ePTFE tube 110 to be plastically deformed by the radial expansion of the inelastic balloon 112, step 222 of FIG. 6A. The terms "plastic deformation" and "plastically deform," as used herein, is intended to include the radial expansion of the ePTFE tube 110 beyond the elastic limit of the ePTFE material such that the ePTFE material is permanently deformed. Once plastically deformed, the ePTFE material forming the tube 110 becomes substantially inelastic, i.e., the ePTFE tube generally will not, on its own, return to its pre-expansion size and shape.

Figure 4C:
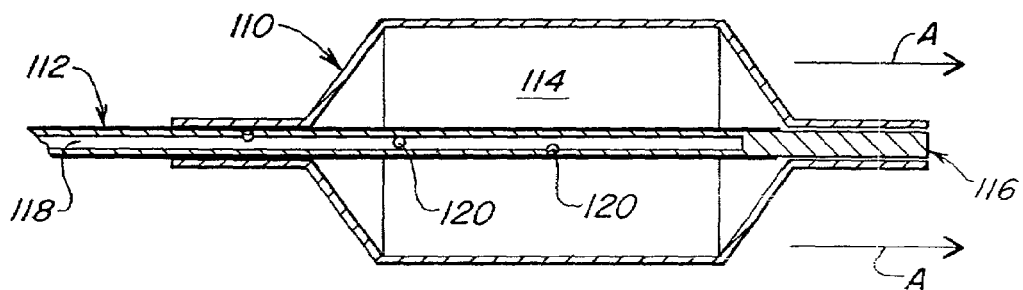
FIG. 4C is a side elevational view in cross-section of the inelastic balloon and the expanded fluoropolymer tube of FIG. 4A, illustrating the removal of the deflated inelastic balloon from the expanded fluoropolymer tube in accordance with a method of manufacturing a radially expandable device according to the teachings of the present invention.

The ePTFE tube 110 can be removed from the balloon 112 by sliding the ePTFE tube 110 relative to balloon 112 and catheter 116, i.e. in the direction of arrows A in FIG. 4C, step 224 of FIG. 6A. The tube 110 can be heat set at a temperature above the sinter point of the material forming the tube, 360° C. for ePTFE, to lock in the structure of the tube 110, step 225 of FIG. 6A.

The resultant radially expanded ePTFE tube 110, produced in accordance with the above described method, provides a radially expandable device having a shaped form, such as expandable device 10 illustrated in FIGS. 1 and 2 and described above, that is radially expandable from a relaxed, collapsed diameter to the second, increased diameter D upon application of a radial deployment force from a deployment mechanism, e.g., hollow tube 20, within the tube 110. The ePTFE tube 110 further provides an expansion device 10 having monolithic construction, that is, a singular, unitary construction of generally homogenous material, ePTFE, that lacks seams or other internal interfaces. The ePTFE tube 110 can be dependably and predictably expanded to the second diameter D upon the application of the radial deployment force within the tube. In particular, the plastically deformed, monolithic microstructure of the ePTFE tube 110, once radially expanded by the inelastic balloon 120, will readily return to the increased diameter D upon application of a radial deployment force and generally will not expand beyond the increased diameter D. The increased diameter D is effectively the maximum expansion diameter for the ePTFE tube, as the increased diameter D is generally independent of the radial deployment force applied to the tube.

Figure 5:
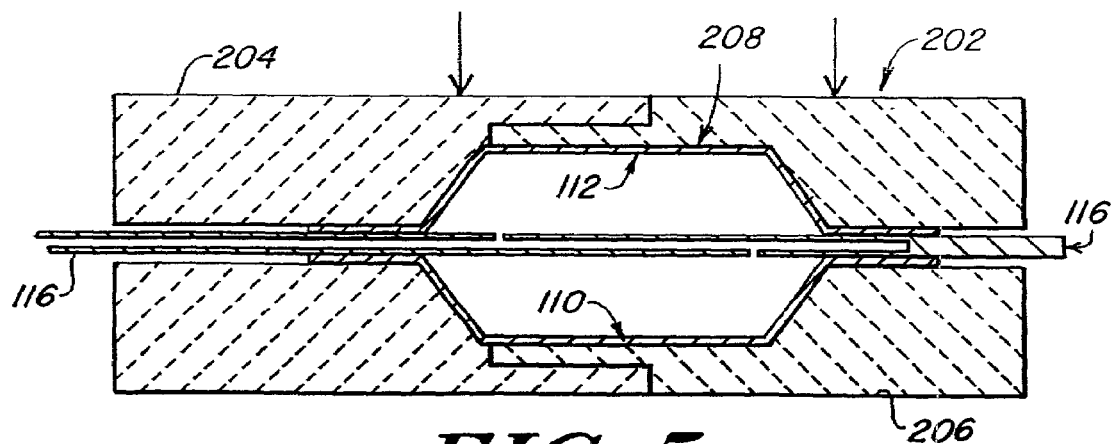
FIG. 5 is a side elevational view of an inelastic balloon and an expanded fluoropolymer tube positioned within the internal cavity of a mold fixture, illustrating the inelastic balloon in a inflated condition in accordance with a method of manufacturing a radially expandable device according to the teachings of the present invention.

Referring to FIG. 5, an alternative method of manufacturing a radially expandable device having a shaped form employing a mold 202 is illustrated. The mold 202 includes two interconnected sections 204 and 206 forming an internal mold cavity 208 for receiving the ePTFE tube 110 with the balloon 112 positioned therein. The mold 202 is preferably constructed of a rigid, unyielding material such as a metal or metal alloy. Suitable metals or metal alloys include brass and steel alloys. The internal mold cavity 208 preferably has a size and shape analogous to that of the inflated balloon 112 to ensure that the inflated balloon 112, and the overlying ePTFE tube 110 concentrically expand.

Figure 6B:
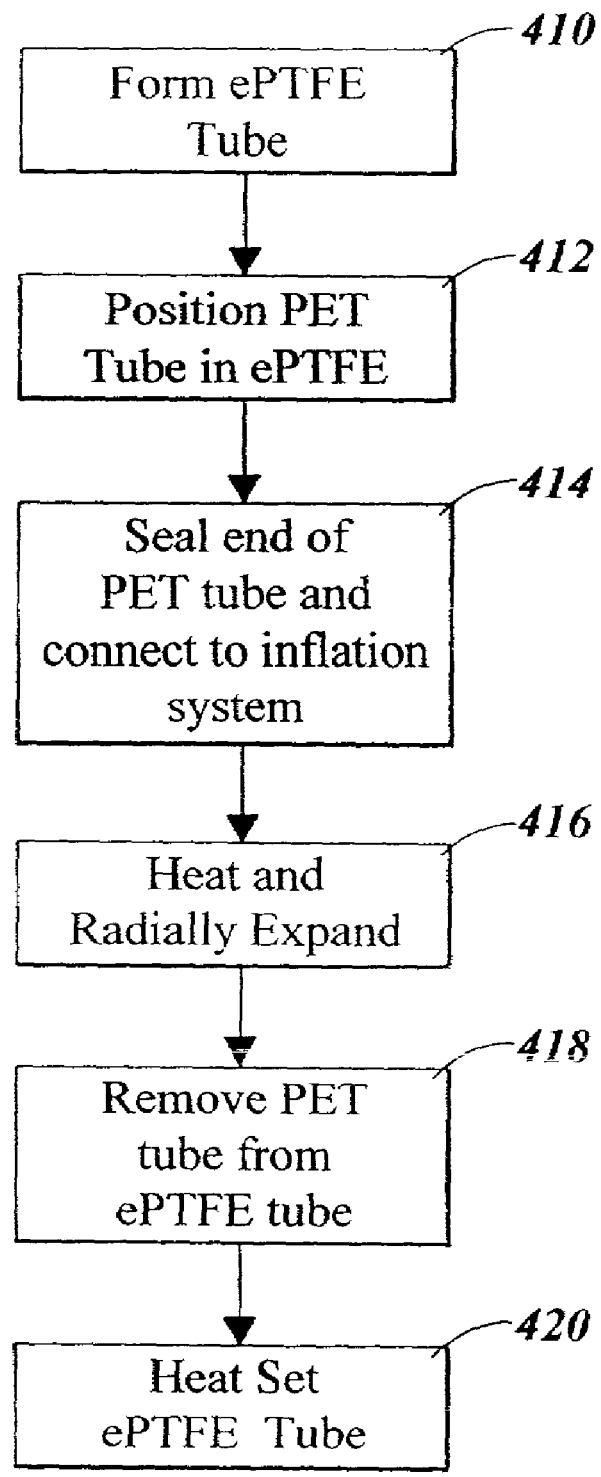
FIG. 6B is a flow chart illustrating the steps of an alternative method of manufacturing a radially expandable device according to the teachings of the present invention.

Referring to the flow chart illustrated in FIG. 6B, a further alternative method of manufacturing a radially expandable device having a shaped form according to the teachings of the present invention will be described. A tube constructed of ePTFE is formed in accordance with the methods described above, step 410. A tube formed of an extruded inelastic material such as PET is used in place of balloon 112 to radially expand the ePTFE tube. The extruded tube is positioned within the ePTFE tube 110, step 412. The extruded tube is then sealed at one end and attached to an inflation system at the other end, step 414. The extruded tube can then be inflated by an inflation medium to radially expand the ePTFE tube, step 416. The extruded tube and ePTFE tube are preferably heated to the glass transition temperature of the extruded tube, approximately 80° C.-100° C. for PET, as the extruded tube is inflated within the ePTFE tube. It is preferable to limit the temperature of the extruded tube to a temperature less than or equal to the glass transition temperature of the material forming the extruded tube to facilitate removal of the extruded tube from the ePTFE tube. Heating the extruded tube to a temperature above the glass transition temperature will cause the extruded tube to heat set in an expanded configuration, which makes removing the extruded tube from the ePTFE tube difficult. A suitable inflation system employing a hot water chamber for heating the tubes is described in Applicants copending U.S. patent application Ser. No. 09/411,797, filed on Oct. 1, 1999, and previously incorporated herein by reference.

After the extruded tube and ePTFE tube are expanded to desired size and shape, the extruded tube is deflated and removed from the ePTFE tube, step 418. The ePTFE tube is then heat set to lock in the structure of the ePTFE tube, step 420.

A mold, such as mold 202, can be employed during radial expansion of the ePTFE tube using the PET tube. The mold is preferably heated within the hot water chamber of the inflation system or by other means such as a hot oil bath or through a steam, hot air, electric, radio frequency or infra red heat source. The mold can be constructed of a material having good heat transfer characteristics, such as metal or metal alloy, for example brass. The mold includes a mold cavity having a size and shape analogous to the desired size and shape of the radially expandable device 10 in the second diameter configuration.

Expansion devices of a wide variety of sizes and shapes may be constructed by altering the geometry of the inelastic balloon 112 or the mold 202. Accordingly, an ePTFE expansion device having a size and shape tailored to a particular function can be manufactured in accordance with the manufacturing methods of the present invention by selecting an inelastic balloon having the desired size and shape. Exemplary expandable fluoropolymer medical treatment devices of different size and shapes are illustrated in FIGS. 7A-7C.

Figure 7A:
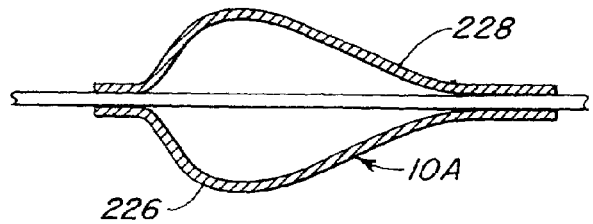
FIG. 7A is a side elevational view in cross section of a generally pear-shaped radially expandable device in accordance with the teaching of the present invention.

FIG. 7A illustrates a radially expandable treatment device 10A having a generally pear-shaped configuration when inflated. The pear shaped configuration is particularly suited for removal of obstructions, such as thrombi and emboli, from a body passage. The expandable treatment device 10A has an increased diameter section 226 that tapers to a reduced diameter section 228. The diameter of the increased diameter section 226 is preferably equal to or slightly less than the diameter of the body passage. The increased diameter section 226 is the primary mechanism for removing obstructions from the body passage and, thus, preferably substantially fills the entire diameter of the body passage to facilitate complete removal of all obstructions from the body passage. The pear-shaped configuration provides the expandable treatment device 10A with a limited, reduced surface area, the increased diameter section 226, which can engage the walls of the body passage and thus minimizes potential damage to the walls of the body passage.

Figure 7B:
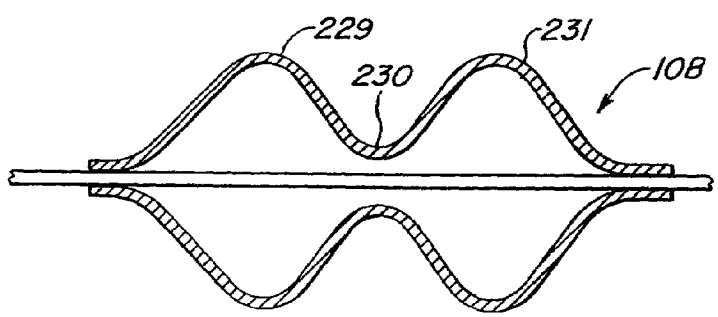
FIG. 7B is a side elevational view in cross section of a generally hour glass shaped radially expandable device in accordance with the teaching of the present invention.
Figure 7C:
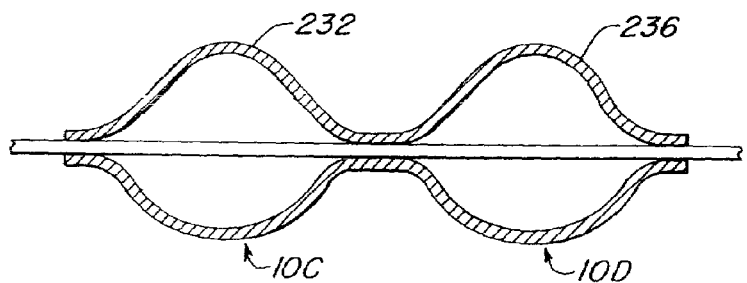
FIG. 7C is a side elevational view in cross section of two coaxially aligned, adjacent radially expandable devices in accordance with the teaching of the present invention.

FIGS. 7B and 7C illustrate alternative exemplary embodiments of the expandable device of the present invention, each providing the device with a reduced surface area for contacting the walls of a body passage. In particular, FIG. 7B illustrates a substantially hour-glass shaped expandable treatment device 10B including, when inflated, a first increased diameter section 229 that tapers to a reduced diameter section 230 that expands to a second increased diameter section 231. As in the case of the exemplary embodiment described above and illustrated in FIG. 7A, the first and second increased diameter sections 229 and 231 preferably have a diameter equal to or slightly less than the diameter of a body passage to be treated to facilitate complete removal of obstructions from the body passage.

FIG. 7C illustrates a third exemplary embodiment in which two axially aligned expandable devices 10C and 10D are provided. As is the case of the second exemplary embodiment described above, the dual expandable devices 10C and 10D together provide a substantially hour-glass configuration that provides the devices with two increased diameter sections 232 and 236.

One feature of the manufacturing processes of the present invention is that the properties of the ePTFE tube 110 forming the expandable device 10 can be manipulated, by varying the extrusion and expansion process parameters, to produce a radially expandable device 10 having different expansion characteristics. For example, the longitudinal stretch ratio of the ePTFE tube 110, i.e., the ratio of final stretched length of the tube to the initial length, and the diametric stretch ratio of the ePTFE tube 110, i.e., the ratio of the final diameter, after longitudinal stretching, and the initial diameter, and the stretch rate can be varied to yield an expansion device having different radial expansion properties. Applicants determined that larger longitudinal stretch ratios, in the order of 2:1 to 3:1, can result in a ePTFE tube having a microstructure characterized by increased internodal distances and interstitial space. Suitable longitudinal stretch ratios can be from 1.1:1 to 10:1. As discussed above, Applicants determined that increased stretch rates yield an ePTFE tube having a fine nodal structure conducive to radial expansion. Expansion devices constructed from ePTFE tubes having such larger longitudinal and/or diametric stretch ratios and which are stretched at increased rates generally require less radial deployment force to expand from the collapsed, reduced diameter configuration to the expanded, increased diameter configuration. Thus, the magnitude of the radial deployment force necessary to expand the ePTFE tube 110 can be pre-selected and manipulated by varying the stretch ratios and stretch rate of the ePTFE tube 110 during the manufacturing process.

In addition to the longitudinal and diametric stretch ratios and the stretch rate, further process parameters can be varied to produce an ePTFE tube 110 having different characteristics. For example, the ePTFE tube 110 can be manufactured to have a porosity that allows for the fluid utilized to radially deploy the ePTFE tube to the expanded configuration to permeate through the walls of the ePTFE tube at a desired flow rate. The process for producing such a microporous ePTFE tube is described in detail in Applicants' copending U.S. patent application Ser. No. 09/411,797, which is incorporated herein by reference.

Figure 8:
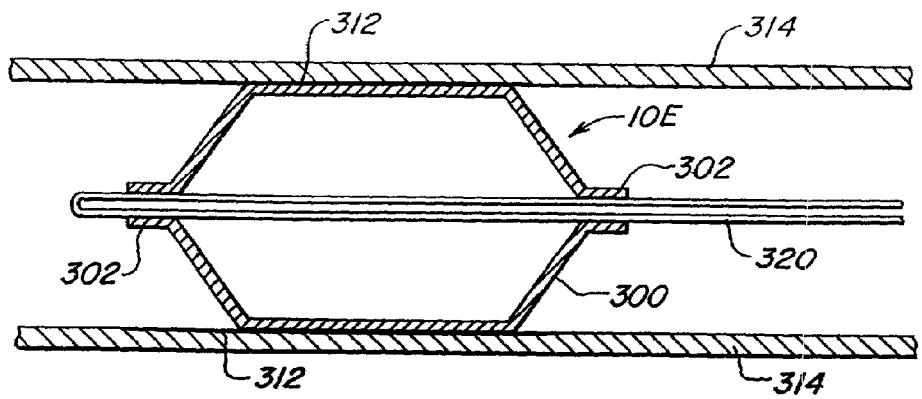
FIG. 8 is a side elevational view in cross section of a catheter deployed dilation balloon according to the teaching of the present invention, illustrating the dilation balloon expanded within a body vessel.

FIG. 8 illustrates an exemplary embodiment of the expandable device of the present invention in which the expandable device 10E is utilized as a catheter deployed dilation balloon 300 for the treatment of a blood vessel 310 partially occluded by plaque deposits 312 adhered to the walls 314 of the blood vessel. The dilation balloon 300 can be manufactured in accordance with the methods of the present invention and is shown in the expanded configuration. The ends 302 of the dilation balloon 300 are bonded to a catheter tube 320, which is used to provide an inflation fluid to the balloon 300 to effect expansion of the balloon 300 to a predefined and fixed maximum diameter.

Figure 9:
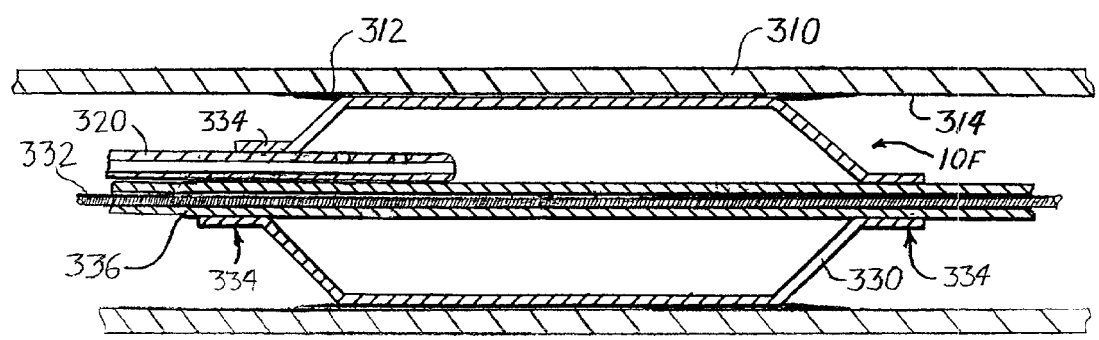
FIG. 9 is a side elevational view in cross section of a catheter deployed dilation balloon deployed with a guide wire, according to one aspect of the present invention.

FIG. 9 illustrates another exemplary embodiment of the expandable device having a shaped form in accordance with the present invention. An expandable device 10F is utilized as a catheter deployed balloon 330 for the treatment of the blood vessel 310 partially occluded by plaque deposits 312 adhered to the walls 314 of the blood vessel 310. The balloon 330 is coupled with a guide wire 332, which guides the balloon 330 into position with a patient body. The balloon 330 can be manufactured in accordance with the methods of the present invention and is shown in the expanded configuration. Ends 334 of the balloon 330 are bonded to a fluid conduit in the form of the catheter tube 320, and also to a guide wire tube 336. The catheter tube 320 is used to provide an inflation fluid to the balloon 330 to effect expansion of the balloon 330 to a predefined and fixed maximum diameter. The guide wire tube 336 is used to channel the guide wire 332 for positioning the expandable device 10F. In accordance with the teachings of the present invention, the inflation fluid can also include one or more drugs for emission to the patient body through the walls of the balloon 330.

The rate at which the fluid emits to the patient body through the walls of the balloon is predetermined to avoid injury to the patient body. For example, the fluid will not spray our jet out of the balloon in a manner that could cause injury due to the hydraulic pressures of the fluid.

One example use for the catheter balloon is in the application of a contrast agent, or dye, for enabling visualization of a body lumen or target location within a patient. The radially expandable device of the present invention provides an occlusive and low pressure flow condition within a body lumen that prevents forward washout flow. The device further provides low pressure perfusion or permeation of the contrast agent or dye to allow for visualization of vessels or other target locations. The combination of the minimal occlusion with the low pressure flow minimizes or mitigates damage due to dissection or wall jetting that might otherwise occur with higher pressure devices. By controlling the porosity and having the ability to vary the channel characteristics through the device walls, the occlusive and low pressure release can be further modified for different structures, vessels, blood flow areas, or other target locations, as understood by one of ordinary skill in the art.

The inclusion of a drug or agent in the fluid passing through the expanded polymer as made possible by the method of manufacture of the present invention eliminates, or at least greatly reduces, systemic responses associated with traditional oral or intravenous therapies. The minimization of drug permeability effects through tissue results from the ability to target the application of the drug or agent to specific locales. The ability to incorporate the drug or agent in the fluid passing through the expanded polymer makes it possible to load the drug delivery system with concentrations significantly greater than known coating technologies. Further, the release of the drug or agent can occur over longer periods of time, i.e. longer dwell time. The use of the expanded polymer including the drug or agent within the fluid passing through provides a material that is radially expandable without splitting or breakage, while still allowing fluid permeation.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

We claim:

1. A radially expandable device having a shaped form, comprising:
    a monolithic balloon body constructed of fluoropolymer material, the fluoropolymer material having a microstructure of nodes interconnected by fibrils, the nodes having an internodal distance of about 1 μm to about 5 μm and oriented to create spaces between the nodes forming channels extending from the inner surface to the outer surface of the wall through which a fluid can flow;
    wherein the body has a structure that enables the body to receive the fluid through a fluid conduit in an amount sufficient to provide a fluid force to expand the body from a reduced diameter collapsed configuration to a pre-defined fixed maximum increased diameter expanded configuration of about the diameter dimension of a body passage diameter in which the device is selected to be implanted; and wherein the microstructure of nodes interconnected by fibrils has a predetermined porosity and structure suitable for regulating a flow of the fluid through the channels at a rate substantially independent of the fluid force as the fluid is introduced for expansion of the body.

2. The device of claim 1, wherein the body can achieve the pre-defined fixed maximum increased diameter prior to the fluid flowing through the microstructure of nodes interconnected by fibrils.

3. The device of claim 1, wherein the fluoropolymer material is expanded polytetrafluoroethylene (ePTFE).

4. The device of claim 1, wherein the body is tubular in shape and wherein the wall extends radially between an inner and an outer surface.

5. The device of claim 1, wherein the fluid flowing through the through-pores has therapeutic characteristics.

6. The device of claim 1, wherein the predetermined porosity comprises a designated porosity for at least a portion of the body.

7. The device of claim 1, wherein the fluid comprises at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

8. The device of claim 1, wherein the fluid comprises at least one of a contrast agent and a dye.

9. The device of claim 1, wherein the fluid can flow through the microstructure of nodes interconnected by fibrils at a rate that will not injure a patient with hydraulic fluid forces.

10. A radially expandable device, comprising:
a monolithic balloon body constructed of fluoropolymer material, the fluoropolymer material having a microstructure of nodes interconnected by fibrils, the nodes having an internodal distance of about 1 µm to about 5 µm and oriented to create spaces between the nodes forming channels extending from the inner surface to the outer surface of the wall through which a fluid can flow;
wherein the body has a structure that enables the body to receive the fluid through a fluid conduit in an amount sufficient to provide a fluid force to expand the body from a reduced diameter collapsed configuration to a pre-defined fixed maximum increased diameter expanded configuration of about the diameter dimension of a body passage diameter in which the device is selected to be implanted; and
wherein the microstructure of nodes interconnected by fibrils has at least two different designated porosities for at least two different portions of the body, such that the at least two different designated porosities are suitable for regulating a flow of the fluid therethrough for at least two different rates substantially independent of the fluid force as the fluid is introduced for expansion of the body.

11. The device of claim 10, wherein the fluoropolymer material is expanded polytetrafluoroethylene (ePTFE).

12. The device of claim 10, wherein the body is tubular in shape and wherein the wall extends radially between an inner and an outer surface.

13. The device of claim 10, wherein the fluid flowing through the through-pores has therapeutic characteristics.

14. The device of claim 10, wherein the predetermined porosity comprises a designated porosity for at least a portion of the body.

15. The device of claim 10, wherein the fluid comprises at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

16. The device of claim 10, wherein the fluid comprises at least one of a contrast agent and a dye.

17. The device of claim 10, wherein the fluid can flow through the microstructure of nodes interconnected by fibrils at a rate that will not injure a patient with hydraulic fluid forces.

18. A drug delivery system, comprising:
a radially expandable balloon having a shaped form, comprising:
a monolithic balloon body constructed of fluoropolymer material, the fluoropolymer material having a microstructure of nodes interconnected by fibrils, the nodes having an internodal distance of about 1 µm to about 5 µm and oriented to create spaces between the nodes forming channels extending from the inner surface to the outer surface of the wall through which a fluid can flow;
wherein the body has a structure configured to receive the fluid in an amount sufficient to provide a fluid force to expand the body from a reduced diameter collapsed configuration to a pre-defined fixed maximum increased diameter expanded configuration of about the diameter dimension of a body passage diameter in which the device is selected to be implanted; and
wherein the microstructure of nodes interconnected by fibrils has a predetermined porosity and structure suitable for regulating a flow of the fluid therethrough at a rate substantially independent of the fluid force as the fluid is introduced for expansion of the body;
a catheter coupled with the radially expandable balloon, the catheter suitable for introducing the fluid to expand the body; and
a guidewire suitable for positioning the balloon within a patient body.

19. The system of claim 18, wherein the fluoropolymer material is expanded polytetrafluoroethylene (ePTFE).

20. The system of claim 18, wherein the body is tubular in shape and wherein the wall extends radially between an inner and an outer surface.

21. The system of claim 18, wherein the fluid flowing through the through-pores has therapeutic characteristics.

22. The system of claim 18, wherein the predetermined porosity comprises a designated porosity for at least a portion of the body.

23. The system of claim 22, wherein the predetermined porosity further comprises at least two different designated porosities for at least two different portions of the body, such that the predetermined porosity is non-uniform.

24. The system of claim 18, wherein the fluid comprises at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

25. The system of claim 18, wherein guidewire is removably and replaceably coupled with the catheter.

26. The system of claim 18, wherein the fluid comprises at least one of a contrast agent and a dye.

27. The device of claim 18, wherein the fluid can flow through the microstructure of nodes interconnected by fibrils at a rate that will not injure the patient body with hydraulic fluid forces.

28. A radially expandable device having a shaped form, comprising:
a monolithic balloon body constructed of a fluoropolymer material, the body having a longitudinal axis and a wall having a thickness transverse to the longitudinal axis and formed of a microstructure of nodes interconnected by fibrils, the nodes having an internodal distance of about 1 µm to about 5 µm and oriented to create spaces between the nodes forming channels extending from the inner surface to the outer surface of the wall through which a fluid can flow, such that the microstructure of nodes interconnected by fibrils has one or more predetermined porosities suitable for regulating the flow of fluid therethrough at one or more substantially constant flow rates for a range of fluid pressures;
wherein substantially all the nodes are oriented generally perpendicularly to the longitudinal axis of the body along at least a portion of the body, the body being deployable from a reduced diameter collapsed configuration to a pre-defined fixed maximum increased diameter expanded configuration of about the diameter dimension of a body passage diameter in which the device is selected to be implanted.

29. The device of claim 28, wherein the fluoropolymer material is expanded polytetrafluoroethylene (ePTFE).

30. The device of claim 28, wherein the body is tubular in shape and wherein the wall extends radially between an inner and an outer surface.

31. The device of claim 28, wherein the fluid flowing through the through-pores has therapeutic characteristics.

32. The device of claim 28, wherein the one or more predetermined porosities comprise a designated porosity for at least a portion of the body.

33. The device of claim 32, wherein the one or more predetermined porosities further comprise at least two different designated porosities for at least two different portions of the body, such that the one or more predetermined porosities is non-uniform.

34. The device of claim 28, wherein the fluid comprises at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, and contrast media.

35. The device of claim 28, wherein the fluid comprises at least one of a contrast agent and a dye.

36. The device of claim 28, wherein the fluid can flow through the microstructure of nodes interconnected by fibrils at a rate that will not injure a patient body with hydraulic fluid forces.

37. A radially expandable device having a shaped form, comprising:
a monolithic balloon body constructed of fluoropolymer material, the fluoropolymer material having a microstructure of nodes interconnected by fibrils, the nodes having an internodal distance of about 1 µm to about 5 µm and oriented to create spaces between the nodes forming channels extending from the inner surface to the outer surface of the wall through which a fluid can flow;
wherein the body has a structure that enables the body to receive a contrast agent or dye through a fluid conduit to expand the body from a reduced diameter collapsed configuration to a pre-defined fixed maximum increased diameter expanded configuration of about the diameter dimension of a body passage diameter in which the device is selected to be implanted; and
wherein the microstructure of nodes interconnected by fibrils has a predetermined porosity and structure suitable for regulating a flow of the contrast agent or dye therethrough at a substantially constant rate independent of fluid force as the contrast agent or dye is introduced for expansion of the body in a manner commensurate with visualizing a target location within a patient.

* * * * *